United States Patent
De Jonge et al.

(10) Patent No.: US 11,499,967 B2
(45) Date of Patent: Nov. 15, 2022

(54) SPECIFIC PROTEIN MARKER AND METHOD FOR IDENTIFYING THE STATISTIC DISTRIBUTION OF PROTEIN STOICHIOMETRY

(71) Applicant: LEIBNIZ-INSTITUT FUER NEUE MATERIALIEN GEMEINNUETZIGE GMBH, Saarbruecken (DE)

(72) Inventors: Niels De Jonge, St. Ingbert (DE); Diana B. Peckys, St. Ingbert (DE)

(73) Assignee: LEIBNIZ-INSTITUT FUER NEUE MATERIALIEN GEMEINNUETZIGE GESELLSCHAFT MIT BESCHRAENKTER HAFTUNG, Saarbruecken (DE)

( * ) Notice: Subject to any disclaimer, the term of this patent is extended or adjusted under 35 U.S.C. 154(b) by 0 days.

(21) Appl. No.: 15/314,150

(22) PCT Filed: Jun. 12, 2015

(86) PCT No.: PCT/DE2015/100238
§ 371 (c)(1),
(2) Date: Nov. 28, 2016

(87) PCT Pub. No.: WO2015/188814
PCT Pub. Date: Dec. 17, 2015

(65) Prior Publication Data
US 2017/0191995 A1 Jul. 6, 2017

(30) Foreign Application Priority Data
Jun. 13, 2014 (DE) ..................... 10 2014 108 331.8

(51) Int. Cl.
*G01N 33/53* (2006.01)
*G01N 33/543* (2006.01)
*B82Y 15/00* (2011.01)

(52) U.S. Cl.
CPC ........ *G01N 33/54346* (2013.01); *B82Y 15/00* (2013.01)

(58) Field of Classification Search
CPC .......................... G01N 33/54346; B82Y 15/00
See application file for complete search history.

(56) References Cited

U.S. PATENT DOCUMENTS

| 4,990,776 | A  | 2/1991  | Fushimi et al.         |
|-----------|----|---------|------------------------|
| 5,811,804 | A  | 9/1998  | Van Blitterswijk et al.|
| 8,604,429 | B2 | 12/2013 | Yaguchi et al.         |
| 2007/0249064 | A1 | 10/2007 | De La Fuente et al. |
| 2011/0284745 | A1 | 11/2011 | Nishiyama et al.    |
| 2012/0025103 | A1 | 2/2012  | Deshmukh et al.     |
| 2012/0120226 | A1 | 5/2012  | De Jonge            |
| 2012/0182548 | A1 | 7/2012  | Harb et al.         |
| 2012/0292505 | A1 | 11/2012 | Damiano et al.      |
| 2013/0200262 | A1 | 8/2013  | Kruit et al.        |
| 2014/0246583 | A1 | 9/2014  | Ominami et al.      |
| 2015/0034822 | A1 | 2/2015  | Reinhorn et al.     |
| 2015/0214001 | A1 | 7/2015  | Buijsse             |
| 2015/0293084 | A1 | 10/2015 | Del Pino González De La Higuera et al. |
| 2017/0205363 | A1 | 7/2017  | De Jonge et al.     |

FOREIGN PATENT DOCUMENTS

| WO | 2004/020453 A2 | 3/2004  |
| WO | 2010/120238 A1 | 10/2010 |
| WO | 2013/151421 A2 | 10/2013 |
| WO | 2014/007624 A1 | 1/2014  |
| WO | 2014/016465 A1 | 1/2014  |

OTHER PUBLICATIONS

Deerinck et al. The application of fluorescent quantum dots to confocal, multiphoton, and electron microscopic imaging. Toxicologic Pathology 2008, vol. 36, pp. 112-116. (Year: 2008).*
Dukes et al. Correlative fluorescence micriscopy and scanning transmission electron microscopy of quantum-dot-labeled proteins in whole cells in liquid. ACS Nano 2010, vol. 4, No. 7, pp. 4110-4116 (Year: 2010).*
Jaiswal et al. Long-term multiple color imaging of live cells using quantum dot bioconjugates. Nature biotechnology 2003, vol. 21, pp. 47-51. (Year: 2003).*
Chang et al. Labeling of neuronal receptors and transporters with quantum dots. Wiley Interdiscip Rev Nanomed Nanobiotechnol 2012, vol. 4, No. 6, pp. 605-619. (Year: 2012).*
International Search Report of PCT/DE2015/100238, dated Oct. 27, 2015.
Kyoung, Lee et al: "Rapid Detection of Intracellular Nanoparticles by Electron Microscopy", Journal of Analytical Science & Technology, vol. 1, No. 1, Jan. 1, 2010, pp. 71-73.
Watanabe, Shigeki et al: "Protein localization in electron micrographs using fluorescence nanoscopy", Nature Methods, vol. 8, No. 1, Jan. 2011, pp. 1-18.
English translation of the International Preliminary Report on Patentability and Written Opinion of the International Searching Authority in PCT/DE2015/100238, dated Dec. 15, 2016.
Peckys et al., Local variations of HER2 dimerization in breast cancer cells discovered by correlative fluorescence and liquid electron microscopy, Research Article, Cell Biology, Sci. Adv. 1:e1500165 (2015), 10 pages.

(Continued)

*Primary Examiner* — Shafiqul Haq
(74) *Attorney, Agent, or Firm* — Collard & Roe, P.C.

(57) ABSTRACT

The present invention relates to a specific protein marker and to a method for identifying the statistical distribution of protein stoichiometry. Novel specific protein markers and methods for their detection are needed in order to clarify important biological questions. This objective is established by means of a specific protein marker comprising two (separate) units, of which
  the first unit comprises a molecule for specifically binding to a protein and at least one chemically coupled molecule for binding to the second unit, and
  the second unit comprises a surface-modified nanoparticle, said surface-modified nanoparticle having a surface coating comprising at least one molecule for binding to the first unit.

9 Claims, 3 Drawing Sheets

(56) References Cited

OTHER PUBLICATIONS

Peckys et al., Studying the Stoichiometry of Epidermal Growth Factor Receptor in Intact Cells using Correlative Microscopy, Journal of Visualized Experiments (2015), 11 pages.
International Search Report in PCT/DE2015/100097, dated Jul. 10, 2015.
International Search Report in PCT/DE2015/100245, dated Oct. 13, 2015.
A. C. Zonnevylle et al., "Integration of a high-NA light microscope in a scanning electron microscope," Journal of Microscopy, vol. 252, Issue 1, 2013, pp. 58-70.
Nalan Liv et al., "Simultaneous Correlative Scanning Electron and High-NA Fluorescence Microscopy," PLOS ONE, Feb. 2013, vol. 8, Issue 2, e55707, total of 10 pages.
Diana B Peckys et al: "Liquid Scanning Transmission Electron Microscopy: Imaging Protein Complexes in their Native Environment in Whole Eukaryotic Cells" Microscopy and Mircoanalysis, Springer, New York, US, vol. 20, No. 2, Apr. 1, 2014, pp. 346-365.
Elisabeth A Ring et al: "Microfluidic System for Transmission Electron Microscopy", Microscopy and Microanalysis, Springer, New York, US, vol. 16, No. 5, Oct. 1, 2010, pp. 622-629.

* cited by examiner

SPECIFIC PROTEIN MARKER AND METHOD FOR IDENTIFYING THE STATISTIC DISTRIBUTION OF PROTEIN STOICHIOMETRY

CROSS REFERENCE TO RELATED APPLICATIONS

This application is the National Stage of PCT/DE2015/100238 filed on Jun. 12, 2015, which claims priority under 35 U.S.C. § 119 of German Application No. 10 2014 108 331.8 filed on Jun. 13, 2014, the disclosure of which is incorporated by reference. The international application under PCT article 21(2) was not published in English.

The present invention relates to a specific protein marker and to a method for identifying the statistical distribution of protein stoichiometry.

Cellular functions are regulated by the molecular mechanisms of proteins, DNA, peptides etc., which are dynamically assembled to form macromolecular complexes. Over the last fifty years, numerous technical advances in biomedical research have been made and valuable insights into complex molecular interactions gained. However, many scientific questions concerning the interplay of macromolecular complexes and cellular functions have not been fully clarified, one of the reasons being the absence of methods for investigating them in intact cells. In consequence, biochemical studies sometimes yield contradictory results. These biochemical studies, moreover, do not provide any information concerning the original location of the macromolecular complexes within the cells.

Furthermore, it is difficult to image cell components within intact cells, because of the nanorange dimensions.

An important issue is the conditions under which and the location at which dimerisation occurs. This example reflects just one of many questions relating to the interplay of approximately 20,000 proteins in a typical eukaryotic cell.

Ideally, a biologist or a biophysicist would have at his disposal a fast microscope with a spatial resolution of a few nanometers in order to identify the sites of individual sub-units in a protein complex. The cell would ideally be located in its natural aqueous surroundings and would not undergo any damage during localisation of the sub-units. Membrane proteins, in particular, which constitute the principal group of modern active-agent targets, are difficult to investigate with the currently known microscopy techniques.

The disadvantages of the commonly used light microscopes are discussed below.

Cellular functions are frequently investigated with fluorescence microscopes, using cells tagged with fluorescent protein markers. Super-resolution fluorescence microscopy generates images with a spatial resolution of a few tens of nanometers. However, the resolution is limited by the various properties of the fluorophore and, in the case of stimulated emission depletion microscopy (STED), the intensity of the laser beam, to such an extent that a value of approx. 30 nm is obtained for practical intact-cell imaging conditions. But this length scale is not sufficient to reflect individual marked proteins in complexes. This is necessary, however, if cellular functions are to be investigated at molecular level. Looking at research on the epidermal growth factor (EGF) membrane receptor (EGFR), for example, it soon becomes evident that techniques are needed for distinguishing whether a receptor exists in a monomeric, dimeric or cluster configuration.

Other technological developments in light microscopy, such as plasmon resonance coupling, total internal reflection fluorescence microscopy (TIRFM) and calibrated single-photon detection, have been used to investigate EGFR and other membrane receptors. It must be kept in mind, however, that spatial resolution is diffraction-limited with these methods, and that they have to rely on comprehensive image processing and computations. These methods do not visualize the individual EGFRs directly. They only permit indirect conclusions as to EGFR ensembles.

Another light-microscopy method, known as Förster resonance energy transfer (FRET), is a highly sensitive method for short intermolecular distances (<10 mil) and has been used successfully to investigate conformational changes in EGFRs. However, FRET, too, is an ensemble average method and must be interpreted with the greatest of care when it comes to the smallest clusters, the dimers. The reason for this is that FRET data indicating dimers can also originate from a mixture of monomers and large clusters (with—on average—two molecules close together).

A further approach is to estimate the number of protein complex sub-units in prepared plasma-membrane patches by means of discolouring the fluorescent signals in discrete steps using time-resolved microscopy. However, this technique necessitates a very low density of the fluorescently labeled protein complex within an area the size of a diffraction stain. It requires stochastic approximations, leads to practical difficulties during the examination of intact cells and is limited to altogether five sub-units of the same type. In addition, the results have to be checked, using biochemical methods or electron microscopy in order to guarantee the accuracy of the interpretation.

Electron microscopy is the method of choice for nanoscale studies. Current nanoscale methods of examining cells usually make use of transmission electron microscopy (TEM) of thin cell sections embedded in plastic, frozen sections, edges of frozen cells or freeze-fractures of cell samples. Alternatively, the cells can be sliced and then imaged in a serial process. In all instances, solid samples are required for investigations within the vacuum of the electron microscope, meaning that the cells do not remain in the liquid state. The contrast and the resolution, moreover, are usually insufficient to permit direct identification of the individual proteins in eukaryotic cells. For this reason, specific immune markers made of heavy materials, e.g. gold nanoparticles (Au-NP), are needed, which are coupled to specific antibodies, in order to localise proteins in thin sections. The nanoparticles (NP) offer sufficient contrast in electron microscopy to enable identification of proteins in the densely packed cell matrix.

A scanning transmission electron microscope (STEM) offers even higher resolution for the imaging of marked proteins embedded in the biological structure. Markers made of heavy materials show up even more strongly in STEM on account of the atomic number (Z) contrast. This principle is used to identify markers in intact cells in a layer of liquid.

Although electron microscopy enables the position of proteins to be established with adequate precision, this type of microscopy is currently limited by the availability of specific markers.

Many researchers therefore use immunogold markers. However, the nanoparticle markers are attached to the proteins under study via fairly long linkers. The linker, consisting, for example, of one or two antibodies, is flexible and typically has a length of 30 nm. As a direct consequence of the linker's length, the exact position of the protein cannot be determined with an accuracy better than 30 nm. This strongly limits the use of these markers.

Immunogold markers provide information on the presence of a specified protein species, for example in an organelle, but cannot provide information on the exact site of the protein with an accuracy better than 30 nm. Any conclusions as to the stoichiometry of the protein complex are thus ruled out. However, this information is important and is needed to investigate protein functions.

A second method used in electron microscopy is marking via a natural ligand for a receptor protein. The ligand is typically a small molecule that binds specifically to a certain receptor. It is bound to a nanoparticle via a relatively short linker (5-10 nm in length). The small size of the ligand and the linker make it possible to draw conclusions as to the protein's dimerisation state. However, this method, too, has its limits. Binding of the ligand frequently triggers a process in the cell that usually leads to conformational changes and hence to a change in the stoichiometric state. Although this method is of interest for certain studies, it is desirable in many other instances to investigate the protein in its initial state (prior to binding of the ligand). Another disadvantage of using natural ligands is that the group of available receptor proteins with (suitable) ligands is limited, meaning that a large group of relevant proteins cannot be labeled by means of this method.

A third technique employed in electron microscopy involves the use of genetically encoded fluorescent markers, which are used to precipitate metal pigment at the site of a protein if the site is irradiated with light of a certain wavelength. But this method, too, is limited in that it requires the cell to have been genetically modified and that the precipitation process only works with dead and fixed cells.

The object of the invention is therefore to overcome the aforementioned drawbacks by providing a novel specific protein marker and a method for its detection by means of electron microscopy.

The object is established by means of a specific protein marker comprising two units, a first unit and a second unit, of which the first unit comprises a small molecule for binding specifically to a protein and at least one chemically coupled molecule for binding to the second unit, and the second unit comprises a surface-modified nanoparticle, said surface-modified nanoparticle having a surface coating comprising at least one molecule for binding to the first unit.

The invention provides for both mists to be available separately prior to their use.

Provision is also made for the small molecule (for binding specifically to a protein) of the first unit to consist of a peptide sequence, a DNA sequence or a small chemical molecule.

The (small) molecule for binding to a specific protein may be composed of a peptide sequence consisting of a maximum of 60 amino acids. The (small) molecule may also be composed of an RNA or DNA sequence consisting of a maximum of 70 nucleotides. The invention furthermore provides for the (small) molecule to be a chemical molecule with a molecular weight not exceeding 12 kDa. The binding affinity of the (small) molecule is in the lower micromolar to the middle picomolar range.

A possible application for the specific protein marker may, by way of example, be its use for detection of the HER2 protein, of new cancer drugs, and as a possible candidate for diagnosing cancer. HER2 is of particular importance for breast cancer, as it is overexpressed in approximately one third of all malignant breast tumours and this correlates significantly with a reduced survival period. A peptide may be used in this instance which is able to bind specifically to HER2 and which is related to the domain of staphylococcal protein A (SPA), which has around 1-13 substitution mutations.

An embodiment of the invention provides for the nanoparticle to consist of a material with a high atomic number (Z).

Elements as from the IV period and elements from the subgroups, including the lanthanoids and the actinoids, are given preference.

The invention provides, in particular, for the nanoparticle to consist of gold (Au), platinum (Pt), another precious metal, or cadmium selenide (CdSe), zinc sulphide (ZnS) or lead selenide (PbSe).

It would also be possible to use, for example, silver (Ag) nanoparticles.

It Is furthermore advantageous for the nanoparticle to be spherical, elliptical or rod-shaped.

It is also within the scope of the invention for the nanoparticle to have a diameter ranging from 0.5 to 15.0 nm.

For binding of the first unit to the second unit, it is advantageous for the coating to contain at least one streptavidin protein and for the chemically coupled molecule to be a biotin protein.

Further possible adhesion molecule linkages may, for example, be amide bonds, gold-sulphur bonds or also van der Waals bonds.

Another embodiment of the invention provides for the nanoparticles to be fluorescent nanoparticles.

For example, the use of CdSe, ZnS, InP or PbSe nanoparticles measuring approximately 10 nm, so-called quantum dots (QDs), is conceivable. Quantum dots of other materials, too, are conceivable and fall within the scope of the invention.

The use of fluorescent nanoparticles is advantageous if a fluorescence-type light microscope is used in addition to an electron microscope for purposes of detection. The markers with the fluorescent nanoparticles may also be used exclusively in combination with a light microscope, in which case marker efficiency and marker specificity would still be improved.

The invention also provides advantageously for the surface coating to be a surfactant coating. This is the case, for example, when the nanoparticles are surface-coated with streptavidin molecules.

A surfactant coating is particularly advantageous for the solution behaviour of the surface-modified nanoparticles in aqueous solutions.

The object of the invention is furthermore established by a method for identifying the statistical distribution, of protein stoichiometry in cells, using the specific protein marker according to claim 1 and comprising the following steps:

a) Cultivating the cells in a suitable medium
b) Incubating the cells with the molecules (small molecule and chemically coupled molecule) of the first unit in the suitable medium
c) Rinsing the cells to remove surplus unbound molecules from the first unit
d) Fixing the cells chemically or thermally
e) Incubating the fixed cells with the second unit, which is in a suitable medium
f) Rinsing the cells to remove surplus unbound molecules from the second unit
g) Micrographing with an electron microscope.

The method for detecting the position of a protein is as follows: The cells or the cell are/is cultivated using methods familiar to qualified technicians. The first unit of the specific protein marker, which contains the specific binding peptide, DNA or RNA sequence, or small chemical molecule, is incubated with the cells in a suitable medium. The concentration of the specific protein marker and the incubation time are optimized for efficient and specific detection. Typically, the specific protein marker is used in a concentration which is two to three orders of magnitude greater than the binding affinity of the ligand to the protein of interest. The incubation time is usually a few minutes. Thereafter, surplus molecules are rinsed off from the first unit of the specific protein marker and the cells are fixed chemically, thermally or physically.

A variant of this method provides for the cells to be incubated in a suitable medium containing substances such as bovine serum albumin, and for non-specific binding of the subsequently employed marker units to be blocked. Incubation with the suitable medium preferably takes place between steps a) and b), i.e. before the cells are incubated with the molecules (small molecule and chemically coupled molecule) of the first unit in the suitable medium.

To fix the cells chemically, they are treated, for example, with paraformaldehyde and a low concentration of glutaraldehyde in order to achieve cross-linking of the proteins, terminate cell processes and preserve the cellular state. Instead of fixing the cells chemically, it is also possible to slow down cell processes using other methods, for example by lowering the temperature (thermal fixation).

It is also conceivable for the cells to be fixed prior to incubation with the first part of the specific protein marker.

After the cells have been incubated with the first unit of the specific protein marker, they are incubated with the second unit of the marker, the surface-modified nanoparticle. Binding of the nanoparticles to the binding sites is usually less efficient than that of the peptides to the protein. The reason for this is the size and mass of the nanoparticles. Other factors encountered in practical experiments are that the concentration of nanoparticles is often limited for cost reasons, and that, at higher concentrations, the nanoparticles may bind non-specifically. However, if the cells are fixed according to the invention, efficient labeling can be obtained by optimizing their incubation, with the second unit of the protein marker, for example by increasing the incubation time to 30 minutes, and/or by adding substances that blanket sites at which the nanoparticles might possibly bind non-specifically.

The specific protein marker of the invention binds to the cells during the course of the experiment by way of the two units, the first and the second unit.

Once the specific protein marker has bound to the cells, the cells can be imaged by way of electron microscopy. The localisation data obtained for the various proteins makes it easy to determine whether they are part of a protein complex or not. Proteins may be present as single proteins, as dimers or in clusters of a higher magnitude. Electron micrograph evaluation and/or localisation, analysis of numerous proteins then provides statistical information on their stoichiometric distribution.

One advantage of the two-stage labeling procedure described above is the achievement of optimal labeling efficiency and marker specificity.

A further important advantage of the method according to the invention is that it enables labeling to be carried out with a nanoparticle having a multiplicity of adhesion molecules, without generating clustering artefacts.

This will now be explained using a counter-example: markers generated from small peptides couple with surface-modified nanoparticles, the surface-modified coating of which has a multiplicity of binding molecules. These are incubated with the cells in a one-stage procedure. If a marker having a multiplicity of binding sites, is incubated with living cells, the marker induces clustering. This is because, following initial binding of a nanoparticle to a protein, neighbouring proteins also couple, by way of diffusion processes, to the available binding sites on the nanoparticle. One nanoparticle thus concentrates a number of proteins. This formation of clusters prevents reliable investigation of the statistical stoichiometric distribution of the target protein species.

If the marker according to the invention and the two-stage procedure are used, the peptide first binds to the target protein. The second unit of the protein-specific marker, which contains the surface-modified nanoparticle, is only applied after the fixation step, meaning that clustering cannot occur. The marker according to the invention can thus be used to identify the stoichiometry.

Another advantage of the sequentially applied units of the protein-specific marker is that greater flexibility is achieved in the experiments.

The object of the invention is also established by a method for identifying the statistical distribution of protein stoichiometry in cells, using the specific protein marker according to claim 1 and comprising the following steps:
a) Coupling, or binding, of the first unit to the second unit
b) Cultivating the cells in a suitable medium
c) Incubating the cells with the first and second units, mutually coupled or bound according to step a), in the suitable medium
d) Rinsing the cells to remove surplus unbound molecules from the first and second units
e) Micrographing with an electron microscope.

For this method of achieving the objective, the invention provides for use of a surface-modified nanoparticle whose surface coating has precisely one specific adhesion molecule. The two units making up the protein-specific marker are combined (joining of the two units) prior to incubation with the cells. Since the marker has only one binding site per nanoparticle, cluster formation is prevented.

The advantage of this method is that the protein-specific marker can be used for living cells and there is no need for fixation.

In a variant of this method, fixation takes place before or after incubation, with the specific protein marker.

The object of the invention is also established by a method for identifying the statistical distribution of protein stoichiometry in cells, using the specific protein marker according to claim 1 and comprising the following steps:
a) Cultivating the cells in a suitable medium
b) Incubating the cells with at least two different first units in the suitable medium
c) Rinsing the cells to remove surplus unbound molecules from the first unit
d) Fixing the cells chemically or thermally
e) Incubating the cells with at least two different second units, which are in a suitable medium and each of which comprises at least one molecule that adheres to one of the first units
f) Rinsing the cells to remove surplus unbound molecules from the second unit
g) Micrographing with an electron microscope.

For this method of achieving the objective, the invention provides for each of two or more different proteins to be labeled specifically with different markers. The invention also provides for each of the second units to comprise at least one molecule that combines specifically with the first unit.

Various short peptide sequences other than those that bind HER2 are known in cancer diagnostics. For example, peptide sequences are known that bind to EGFR or HER3. All three proteins are highly relevant for cancer diagnosis and cancer therapy.

The second unit of the protein-specific markers may be identified in micrographs via the kind of nanoparticle used. For example, the nanoparticles may be 1.4 nm, 5 nm or 10 nm in size. They may be spherical elliptical or rod-shaped, or made of different materials, such as gold, platinum, CdSe/ZnS or PdSe. The target proteins are identified and localised on the basis of the differences in the nanoparticles (size, shape, material, etc.) in the different specific protein markers. Where fluorescent nanoparticles are used, for example quantum dots (QDs), a photo-optical signature is available in addition.

A combination of specific protein markers makes it possible to recognize and evaluate the stoichiometry of protein, complexes consisting of various kinds of proteins. In consequence, biological researchers are able to clarify an important question concerning the mechanisms involved in the development of breast cancer, namely at what concentration EGFR-HER2 heterodimers are formed and at what concentration their formation is inhibited.

Cell fixation in step d) may be chemical or thermal. To fix the cells chemically, they are treated, for example, with paraformaldehyde and a low concentration of glutaraldehyde in order to achieve cross-linking of the proteins, terminate cell processes and preserve the cellular state. Instead of fixing the cells chemically, it is also possible to slow down cell processes using other methods, for example by lowering the temperature (thermal fixation).

A variant of this method comprises the sequential processing of the different units, i.e. incubation with the first unit of a marker, rinsing, incubation with the first unit of a second marker, fixation, etc. It is also conceivable for the cells to be fixed following incubation with the first unit.

The object of the invention is also established by a method for identifying the statistical distribution of protein stoichiometry in cells, using at least one specific protein marker and a modified natural receptor ligand that can be coupled with a nanoparticle, the method comprising the following steps:

a) Cultivating the cells in a suitable medium
b) Incubating the cells with modified natural receptor ligands in the suitable medium, each of said modified natural receptor ligands having at least one binding site for nanoparticles
c) Rinsing the cells to remove surplus unbound natural receptor ligands
d) Fixing the cells chemically or thermally
e) Incubating the fixed cells with the surfaces-modified nanoparticles, each of the nanoparticles having a surface coating with at least one coupling site for the receptor ligand.
f) Rinsing the cells to remove surplus unbound nanoparticles
g) Incubating the cells with the first unit in a suitable medium
h) Rinsing the cells to remove first-unit surplus
i) Incubating the cells with the second unit, which is in a suitable medium
j) Rinsing the cells to remove second-unit surplus
k) Micrographing with an electron microscope.

According to this solution, the protein-specific marker is combined with a marker that contains a natural receptor ligand.

Cell fixation in step d) may be chemical, thermal or physical. To fix the cells chemically, they are treated, for example, with paraformaldehyde and a low concentration of glutaraldehyde in order to achieve cross-linking of the proteins, terminate cell processes and preserve the cellular state. Instead of fixing the cells chemically, it is also possible to slow down cell processes using other methods, for example by lowering the temperature (thermal fixation).

By way of example, the EGFR dimer may be studied using two different markers: a gold-nanoparticle marker which is attached to the EGF ligand, and, as additional marker, a small binding peptide which is bound to a quantum dot (QD).

To start with, the cells are incubated with EGF and the binding peptide. Thereafter, the cells are fixed. Nanoparticles are then coupled to the ligands, for example through use of EGF-biotion and nanoparticle-streptavidin. It is also possible, for example, to couple the nanoparticle to the EGF prior to incubation. The specific protein marker consisting of two units now comes into use as the second marker, the two units being used sequentially.

However, a nanoparticle other than the nanoparticle coupled to the ligands is used so that ligands and protein may be detected separately.

A QD is coupled, for example, to the EGF ligand and, by means of the specific two-unit protein marker, a gold nanoparticle is coupled to the EGFR protein. Since binding to the ligand activates the EGFR protein, the receptors that have been activated can be localised by means of the QDs. The gold nanoparticles, by contrast, localise all EGFRs.

This makes it possible to answer the important biological question of whether all dimers contain activated EGFRs or whether—and if yes, how many—EGFRs already exist in inactive form as dimers.

In other variants of this method the steps listed above may also be performed in different sequences. For example, the specific protein marker consisting of two units may be used for initial labeling, followed by labeling by means of the natural ligand. However, it is also envisaged within the scope of the invention that the natural ligands and the first unit of the specific protein marker be used simultaneously.

The invention furthermore provides for imaging of the cells in which different proteins have been labeled with specific two-unit protein markers.

The electron microscope used for this purpose may be a transmission electron microscope, a scanning transmission electron microscope or a scanning electron microscope.

The invention also provides for micrographing by means of a device for scanning transmission electron microscopy (STEM), where a STEM detector sensitive to atomic number, referred to as z-contrast is used. Thanks to the STEM detector, the markers or labels show up much more distinctly in the images than does the surrounding cell material.

Provision is furthermore made within the scope of the invention for the markers to be detected in the images manually or via an automated process, thereby providing information on the positions and types of labeled proteins. This data can be evaluated for a plurality of different experiments and then compared, making it possible, for example, to identify whether the prevalence of EGFR dimers is affected by administration of a cancer drug.

The invention furthermore provides for the generation of light-microscopy images of the cells concerned.

This information may be correlated with the positions and types of labels, thereby enabling identification, for example, of areas with a certain labeling pattern.

It is also within the scope of the invention to combine fluorescence-microscopy images and electron-microscopy images of the specific two-unit protein markers. For example, the exact positions of QD-labeled proteins may be compared with the occurrence, in fluorescence-microcopy images, of fluorescence with a wavelength corresponding to that of the QD. This information may be used to identify the cells or cellular regions containing a certain protein. It may also be used to study whether there are local variations in the density/incidence of dimers, both between different cells and within single cells.

It is additionally possible to conduct a time-resolved, investigation of a living cell by means of light and fluorescence microscopy and thus to investigate cellular processes. As soon as a given process has reached a given stage, a specified phase of the labeling or fixation procedure is initiated so that the marker information correlates temporally with a cellular process. The exact time of labeling following administration of an active agent, e.g. a carcinostatic drug, may also be determined in this way.

The invention also provides for micrographing by means of a device for correlative scanning transmission electron microscopy (STEM) and light microscopy, where a STEM detector is combined with a light-optical lens.

This detection device combines efficient STEM-microscopy detection of materials with high atomic numbers, for example specific nanoparticle markers in a specimen contained in a liquid, such as a cell, with simultaneous light microscopy, for example via fluorescence contrast of fluorescent protein markers in cells or via scatter contrast of the cell material. The use of a device of this kind permits extremely efficient detection, with the maximum possible resolution, of materials with a high atomic number in the sample as well as completely time-correlative light microscopy.

A preferred embodiment of the device consists in that the STEM detector is integrated in a light-optical lens.

In this context, it is to advantage that the STEM detector is positioned in a cavity in the light-optical lens.

The device may be configured such that the cavity has, at the specimen end, a small-diameter opening followed by a conical electron drift chamber at the bottom end of which the STEM detector is located.

"Bottom" refers here to an electron beam direction from top to bottom. Arbitrary beam directions are possible depending on how the device is set up. This means that the opening is located at the lens end which is nearer the specimen holder. Following on from the opening is the conical electron drift chamber, which widens out in the downward direction. The STEM detector is located at the bottom end of the electron drift chamber.

The signal from the STEM detector can be transmitted to the outside at the side of the lens.

The device may be provided with a specimen holder located at that end of the light-optical lens which is nearer the specimen, the specimen holder being configured as a thin, electron-permeable membrane.

For purposes of micrographing by means of a device for correlative scanning transmission electron microscopy (STEM) and light microscopy, the electron drift chamber and the space surrounding the specimen holder should have the property of being able to establish a vacuum.

For purposes of micrographing by means of a device for correlative scanning transmission electron microscopy (STEM) and light microscopy, provision may also be made for an electron-beam source to be located on the other side of the specimen holder from the STEM detector.

The detection device may also have a lens to which a light source and light-optical detection means are connected.

The lens with the integrated STEM detector may be installed in different kinds of electron microscopes, e.g. an ESEM with typical electron energy of 30 keV or a high-resolution STEM with typical electron energy of 200 keV.

It is advantageous if the detection device for correlative scanning transmission electron microscopy and light microscopy is provided with one or more other light-optical beam paths for purposes of detection or illumination.

It is also possible, for purposes of micrographing by means of a device for correlative scanning transmission electron microscopy and light microscopy, for the light source to be fitted at the side of the STEM detector, the focus of the light beam to overlap with the electron beam and the light-optical detection path to overlap with the illumination beam.

It would also be possible, for purposes of micrographing by means of a device for correlative scanning transmission electron microscopy and light microscopy, to use a device in which the STEM detector is positioned between the optical lens and the specimen. In the same way, it is possible for the STEM detector to be movable in the area between the optical lens and the specimen.

The prior art and an embodiment of the invention are explained below by reference to drawings.

The drawing in

Figure 1:
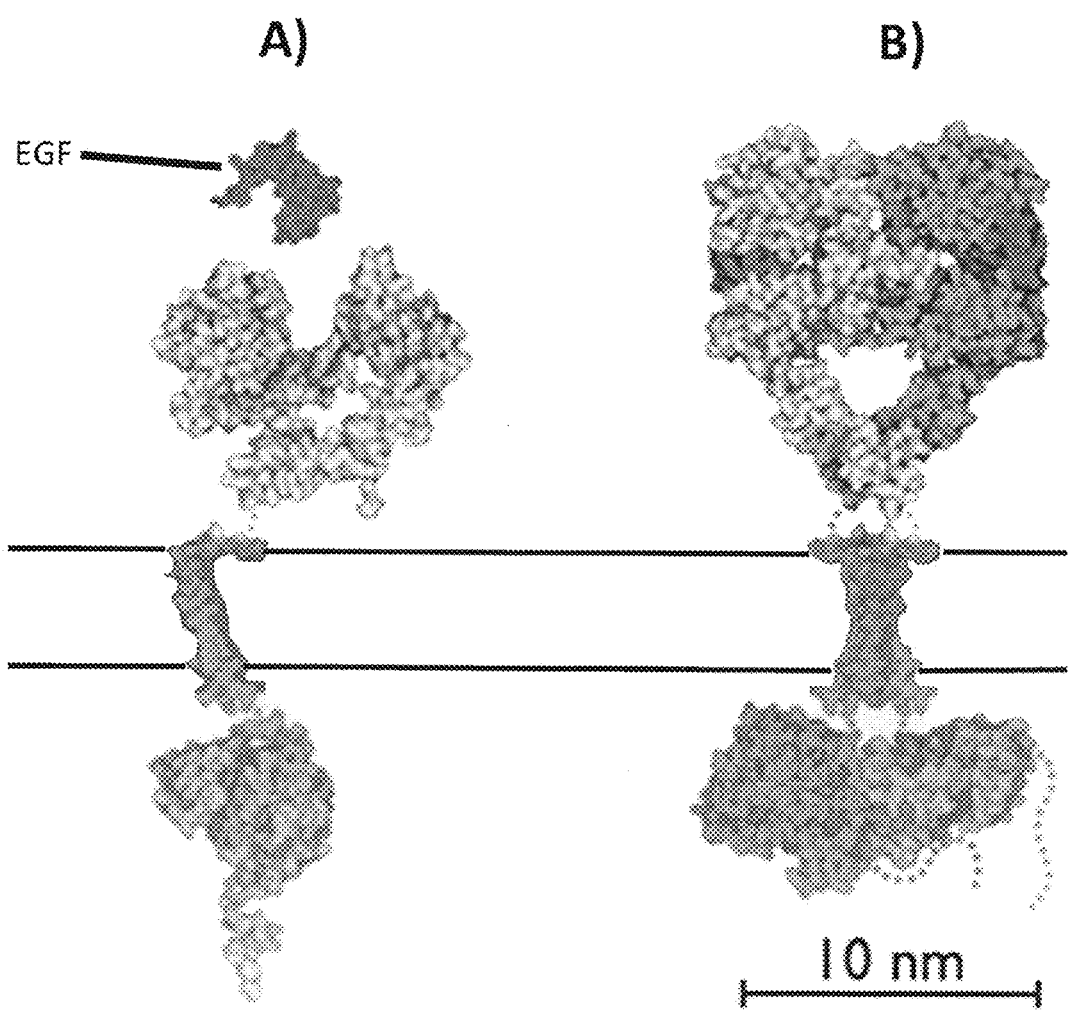
FIG. 1 is a partially schematic representation showing the distance at which proteins interact to form a dimer (here EGFR)

FIGS. 1 A) and 1 B) show an epidermal growth factor receptor (EGFR) in dimer form in the plasma membrane. FIG. 1 A) shows a non-activated EGFR and an unbound epidermal growth Factor (EGF). FIG. 1 B) shows an active EGRF dimer with a bound EGF ligand. FIG. 1 B) shows, by way of example, the distance at which proteins interact to form the epidermal growth factor receptor (EGRF) dimer. The epidermal growth factor plays a crucial role in the pathogenesis and development of many different forms of cancer.

Figure 2:
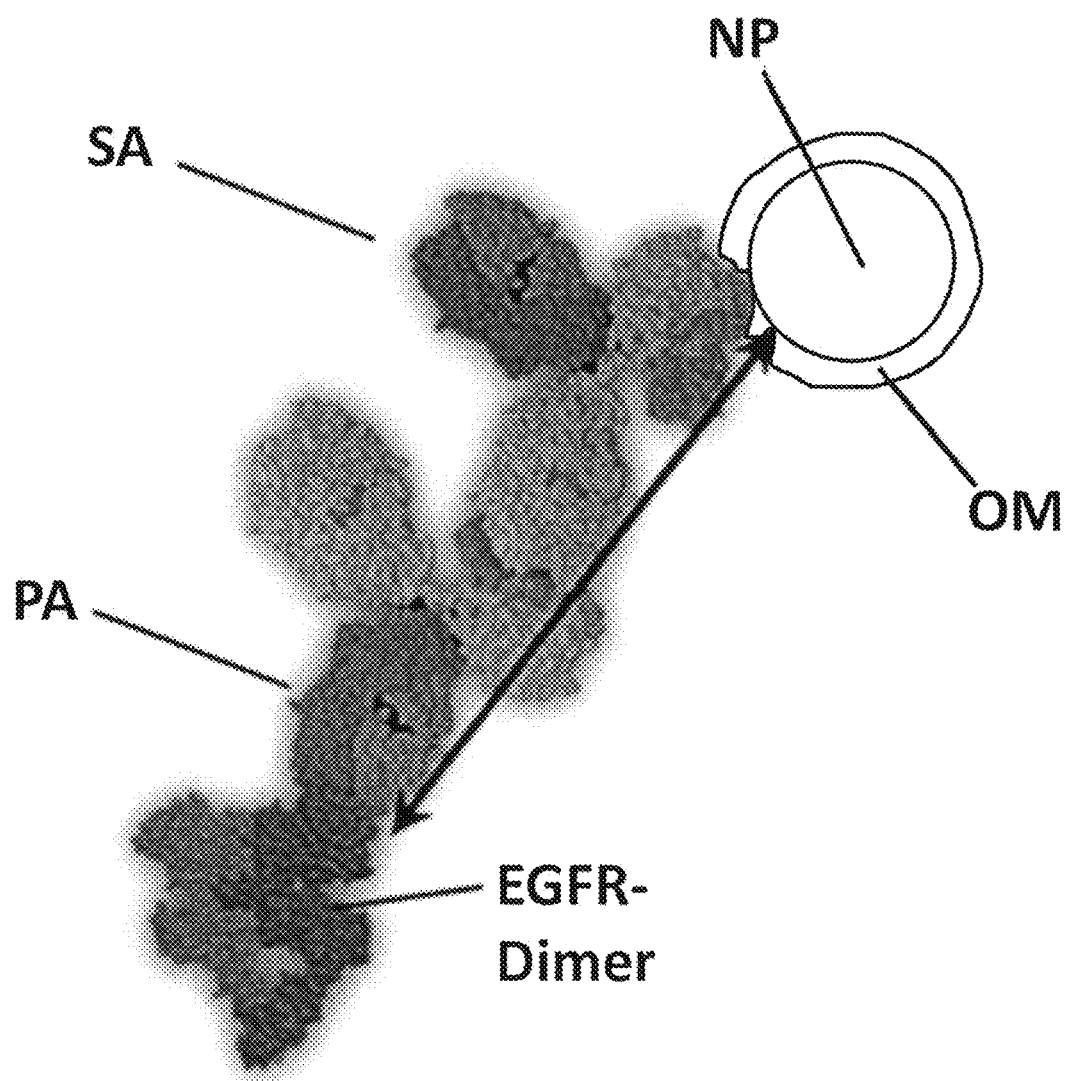
FIG. 2 is a partially schematic representation showing the use of a gold nanoparticle bound via a linker to a target protein (EGFR dimer)

FIG. 2 shows an EGFR dimer which is connected to a gold nanoparticle (NP) via an antibody linker consisting of a primary antibody (PA) and a secondary antibody (SA). The primary antibody (PA) binds specifically to the protein (EGFR) and the secondary antibody (SA) to a gold nanoparticle (NP), the modified surface (OM) of which has at least one chemical molecule for binding to the antibody. The distance (arrow) between the nanoparticle (NP) and the protein (EGFR dimer) may be up to 30 nm.

These immunogold markers are used in many studies. However, the nanoparticle markers are attached to the target proteins via a fairly long linker (see FIG. 2, SA+PA). The linker is flexible and typically has a length of 30 nm. As a direct consequence of the linker length, it is not possible to determine the exact position of the protein (EGFR), or of the two protein components in the case of the EGFR dimer, more accurately than 30 nm, or 60 nm for the dimer. This strongly limits the use of such markers. Immunogold markers provide information on the presence of a specified protein species, for example, in an organelle, but cannot provide information on the exact site of the protein with an accuracy better than 30 nm. In the extreme case, two neighbouring nanoparticles (NP) would show two EGFRs spaced apart by a maximum distance of 60 nm. This distance would be substantially greater than the size of a protein complex. It is thus impossible to conclude from the data whether two observed neighbouring markers show up a dimer or perhaps two proteins with a substantial distance between them. Shorter linker antibodies, which are twice as small, do exist but are seldom used because the distance is still too large for identifying the stoichiometry.

Figure 3:
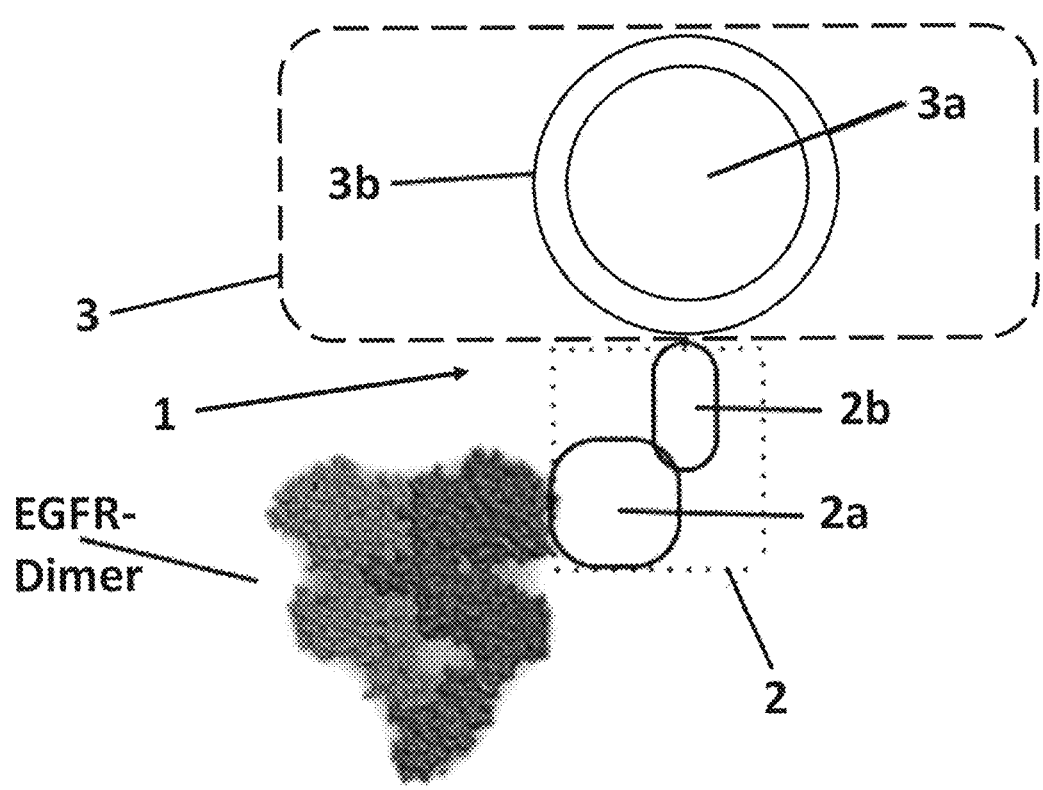
FIG. 3 is a partially schematic representation of the specific protein marker according to the invention, which is bound to an EGFR dimer.

FIG. 3 shows the specific protein marker (1) according to the invention. The drawing shows, by way of example, an EGFR dimer to which the specific protein marker (1) of the invention binds for purposes of identifying the dimer by electron microscopy. The peptide sequence (2a) is coupled with a small molecule (2b), which binds to the surface coating (3b) of a surface-modified nanoparticle (3a). The specific protein marker (1) consists of two parts: the binding peptide (2a) and the small molecule (2b) form a first part (dotted area 2) and the surface-modified nanoparticle (3a), with its surface coating (3b), forms the second part (dashed area 3).

The invention claimed is:

1. A method for identifying a statistical distribution of protein stoichiometry of a protein in cells consisting of the following steps in the following order:
   a) Cultivating the cells in a suitable medium;
   b) Incubating the cells with a first unit in the suitable medium, wherein the first unit comprises a molecule for binding specifically to the protein of the cell and at least one chemically coupled molecule for binding to a second unit, and wherein the molecule for binding specifically to the protein of the cell is composed of a peptide sequence of a maximum of 60 amino acids wherein the protein of the cell is HER2, EGFR or HER3;
   c) Rinsing the cells;
   d) Fixing the cells chemically or thermally;
   e) Incubating the fixed cells with the second unit, said second unit being in a suitable medium, wherein the second unit comprises a surface-modified nanoparticle, said nanoparticle having a surface coating comprising at least one molecule for binding to the chemically coupled molecule of the first unit, wherein the surface coating contains at least one streptavidin protein and wherein the chemically coupled molecule is a biotin;
   f) Rinsing the cells;
   g) Micrographing with an electron microscope;
   h) Determining statistical information on whether the protein is part of a protein complex or not; and thereby
   i) Measuring the protein stoichiometry of the protein of the cell in the cells.

2. A method for identifying a statistical distribution of protein stoichiometry of at least two proteins in cells consisting of the following steps in the following order:
   a) Cultivating the cells in a suitable medium;
   b) Incubating the cells with at least two different first units in the suitable medium, wherein each of the first units comprises a molecule for binding specifically to one protein and at least one chemically coupled molecule for binding to a second unit, and wherein the molecule for binding specifically to one protein is composed of a peptide sequence of a maximum of 60 amino acids, and wherein the protein of the cell is HER2, EGFR or HER3;
   c) Rinsing the cells;
   d) Fixing the cells chemically or thermally;
   e) Incubating the cells with at least two different second units, said second units being in a suitable medium and each of said second units comprising at least one molecule that adheres to one of the first units, wherein each of the second units comprises a surface-modified nanoparticle, said nanoparticle having a surface coating comprising at least one molecule for binding to the chemically coupled molecule of the first unit, wherein the surface coating contains at least one streptavidin protein and wherein the chemically coupled molecule is a biotin;
   f) Rinsing the cells;
   g) Micrographing with an electron microscope;
   h) Determining statistical information on whether the proteins are part of a protein complex or not; and thereby
   i) Measuring the protein stoichiometry of the proteins of the cell in the cells.

3. A method for identifying a statistical distribution of protein stoichiometry of proteins in cells consisting of the following steps in the following order:
   a) Cultivating the cells in a suitable medium;
   b) Incubating the cells with modified natural receptor ligands in the suitable medium, each of said modified natural receptor ligands having at least one binding site for nanoparticles;
   c) Rinsing the cells;
   d) Fixing the cells chemically or thermally;
   e) Incubating the fixed cells with the surface-modified nanoparticles, each of the nanoparticles having a surface coating with at least one coupling site for the receptor ligand;
   f) Rinsing the cells;
   g) Incubating the cells with a first unit in the suitable medium, wherein the first unit comprises a molecule for binding specifically to a protein of the cell and at least one chemically coupled molecule for binding to a second unit, and wherein the molecule for binding specifically to the protein of the cell is composed of a peptide sequence of a maximum of 60 amino acids, and wherein the protein of the cell is HER2, EGFR or HER3;
   h) Rinsing the cells;
   i) Incubating the cells with the second unit, said second unit being in a suitable medium, wherein the second unit comprises a surface-modified nanoparticle, said nanoparticle having a surface coating comprising at least one molecule for binding to the chemically coupled molecule of the first unit, wherein the surface coating contains at least one streptavidin protein and wherein the chemically coupled molecule is a biotin;
   j) Rinsing the cells;
   k) Micrographing with an electron microscope;
   l) Determining statistical information on whether the proteins are part of a protein complex or not; and thereby
   m) Measuring the protein stoichiometry of the proteins of the cell in the cells.

4. The method according to claim 1, wherein, prior to their incubation with the first unit, the cells are incubated in a suitable medium containing substances that block non-specific binding of the second unit.

5. The method according to claim 1, wherein the electron microscope comprises a STEM detector.

6. The method according to claim 1, wherein at least one of a light microscope and a fluorescence microscope is used to generate light-microscopy images and/or fluorescence-microscopy images.

7. The method according to claim 1, wherein the method encompasses the capturing of at least one time-resolved sequence of light-microscopy and/or fluorescence-microscopy images, enabling at least one point in time of at least one of the procedural steps to be correlated temporally with the light-microscopy or fluorescence-microscopy information.

8. The method according to claim 1, wherein a device for correlative scanning transmission electron microscopy (STEM) and light microscopy is used for generating electron-microscopy images, which combines a STEM detector with a photo-optical lens.

9. The method according to claim 1, wherein the distribution is a distribution of EGFR dimers.

* * * * *